United States Patent [19]

Wang et al.

[11] Patent Number: 5,912,325

[45] Date of Patent: *Jun. 15, 1999

[54] BIOLOGICALLY ACTIVE PORCINE SOMATOTROPIN POLYPEPTIDES AND METHODS OF USING THE SAME

[75] Inventors: Bosco Shang Wang, Cranbury, N.J.; Hong-Ming Shieh, Longhorne, Pa.; Martin John Corbett, Mt. Holly, N.J.

[73] Assignee: American Cyanamid Company, Parsippany, N.J.

[ * ] Notice: This patent is subject to a terminal disclaimer.

[21] Appl. No.: 08/222,987

[22] Filed: Apr. 5, 1994

Related U.S. Application Data

[62] Division of application No. 07/922,523, Jul. 29, 1992, Pat. No. 5,338,836.

[51] Int. Cl.$^6$ .................................................. C07K 14/61
[52] U.S. Cl. ........................... 530/399; 530/300; 530/324
[58] Field of Search ..................................... 530/350, 399, 530/300, 324; 514/2, 14, 15; 424/184.1, 198.1

[56] References Cited

U.S. PATENT DOCUMENTS 5,338,836   8/1994   Wang et al. ............................. 530/399

FOREIGN PATENT DOCUMENTS

| 0 429 788 | 6/1991 | European Pat. Off. . |
| 0 593 857 | 4/1994 | European Pat. Off. . |
| 94 04187 | 3/1994 | WIPO . |
| 94 05697 | 3/1996 | WIPO . |

OTHER PUBLICATIONS

Pell J.M., et al., Active Immunication with a Synthetic Peptide Region of Growth Hormone: Increased Lean Tissue Growth Cited in the Application, Journal of Endocrinology, vol. 131, No. 1, Oct. 1991, pp. R1–R4.

Shieh, H–M et al, Epitope mapping and analysis of a growth–enhancing monoclonal antibody by limited tryptic digestion of procine GH, Journal of Endocrinolgy, Vo. 145, No. 1, Apr. 1995, pp. 169–174.

Aston et al. 1991 Mol. Immunol. 28(1/2):41–50.

Wang et al. 1990 J. Endocrinol. 127:481–485.

*Primary Examiner*—Karen Cochrane Carlson
*Attorney, Agent, or Firm*—Darryl L. Webster; Gale F. Matthews; Alan M. Gordon

[57] ABSTRACT

An isolated polypeptide corresponding to the epitope of porcine somatotropin is provided by this invention as well as methods of enhancing the growth of an animal by administering to the animal this polypeptide in compositions.

2 Claims, 7 Drawing Sheets

BIOLOGICALLY ACTIVE PORCINE SOMATOTROPIN POLYPEPTIDES AND METHODS OF USING THE SAME

This is a divisional of application Ser. No. 07/922,523 filed on Jul. 29, 1992, now U.S. Pat. No. 5,338,836.

BACKGROUND OF THE INVENTION

Throughout this application, various publications are referred to within parenthesis and within this specification to more fully describe the state of the art to which this invention pertains. The disclosures of these publications are hereby incorporated by reference into the present disclosure.

Somatotropin is a polypeptide secreted by the anterior pituitary in warm-blooded animals and acts through specific cell surface receptors located primarily in the liver (Hughes, J. P. and Friesen, H. G., Ann. Rev. Physiol., 47, 469–482 (1985)). Somatotropin (i.e., growth hormone) is useful to enhance growth of such animals as bovine (cattle), porcine (pigs, "pST"), caprin (goat), avian (chicken, turkey, geese, etc.) and rabbit, among others. Somatotropin is also useful to enhance the growth of other vertebrates, such as fish.

Specifically, the growth hormone PST is native to swine and accounts for maturation of the animal, including increasing the growth rate and the lean to fat ratio. It has been found that pST is a single chain polypeptide of 191 amino acids with two cystine bridges linking residues 53–164 and 181–189, respectively (Abdel-Meguid, S. S., et al., Proc. Nat. Acad. Sci., 84 6434–6437 (1987).

Because endogenous amounts of pST are small, efforts have focused on the preparation of exogenous pST for use in large-scale agriculture. Efforts have also been directed to the identification of small portions of the pST molecule, the generation of antibodies to those portions, and the administration of those antibodies together with pST to enhance growth. (See, for example, published European Patent Application 284,406). This specification is directed to the administration of fragments of the pST molecule to enhance growth.

SUMMARY OF THE INVENTION

An isolated polypeptide corresponding to the epitope of pST is provided by this invention and compositions containing this polypeptide. This invention also provides methods of enhancing the growth of an animal by administering to the animal this polypeptide.

DETAILED DESCRIPTION OF THE INVENTION

This invention provides an isolated polypeptide corresponding to the epitope for porcine somatotropin (pST). More specifically, this epitope is the binding region reactive with monoclonal antibody PS-7.6. Monoclonal antibody PS-7.6 is deposited with the American Type Culture Collection (ATCC), 12301 Parklawn Drive, Rockville, Md. 20852 U.S.A., under the provisions of the Budapest Treaty on the International Recognition of the Deposit of Microorganisms for the Purposes of Patent Procedure and is allocated ATCC Designation HB 10416. As used herein, the term "polypeptide" encompasses any naturally occurring allelic variant thereof as well as manmade recombinant forms, i.e., non-naturally occurring forms of the polypeptide which are sufficiently identical to naturally occurring polypeptide to allow possession of similar biological activity—such as derivatives and analogues. Any of these polypeptides are made by recombinant systems or a vector engineered to produce these polypeptides as well as made by chemical synthesis.

As is known to those of skill in the art, an epitope is that portion of the antigen molecule, in this case porcine somatotropin polypeptide, that is responsible for the specificity of the antigen in an antigen-antibody binding site to which it is complementary. In one embodiment of this invention, the isolated somatotropin polypeptide has the amino acid sequence shown in FIG. 5 from about amino acid number 50 to amino acid number 105. However, in a preferred embodiment, the isolated somatotropin polypeptide has the amino acid sequence shown in FIG. 5 from about amino acid number 54 to about amino acid number 95. In the most preferred embodiment, the polypeptide has the amino acid sequence shown in FIG. 5 from about amino acid 80 to about amino acid 90.

Sufficiently identical polypeptides includes polypeptides that have an amino acid sequence that is substantially the same as native PST but for small nucleic acid changes that alter the primary structure of the polypeptide. The nucleic acids that encode these polypeptides are able to hybridize to the nucleic acid that encodes native pST under conditions of moderate to high stringency. Methods of hybridization are well known to those of skill in the art. The resultant polypeptide, although altered, is still able to bind to antibody PS-7.6.

This isolated somatotropin polypeptide is isolated from porcine (pigs).

This invention also encompasses the nucleic acid molecules which encode the polypeptides described hereinabove. As used herein, the term "nucleic acid" encompasses RNA as well as single and double-stranded DNA and cDNA. Examples of such nucleic acids are the nucleic acids which encode the polypeptide having the sequence shown in FIG. 5 from amino acid number 54 to amino acid number 105. Nucleic acid molecules which differ from that of the above-identified molecules but which encode polypeptides that produce the same biological effect are encompassed by this invention. And this invention encompasses nucleic acid molecules characterized by changes in non-coding regions that do not alter the phenotype of the polypeptide produced therefrom when compared to the nucleic acid molecules described hereinabove. These nucleic acids are isolated from natural sources or chemically synthesized.

These nucleic acid molecules are inserted into an expression vector for production of the polypeptides biosynthetically. Suitable vectors include, but are not limited to a plasmid, viral or cosmid vector. These vectors comprise the nucleic acids of this invention operatively linked to a promoter of RNA transcription, as well as other regulatory sequences. As used herein, the term "operatively linked" means positioned in such a manner that the promoter directs the transcription of RNA off of the nucleic acid molecule. Examples of such promoters are SP6, T4 and T7. Vectors which contain both a promoter and a cloning site into which an inserted piece of nucleic acid is operatively linked to that promoter are well known in the art. Preferable, these vectors are capable of transcribing RNA in vivo or in vitro. These vectors are inserted into a host cell for the production of the polypeptides. For the purposes of this invention, a suitable host is, but is not limited to, a eucaryotic cell, e.g., a mammalian cell or yeast cell, or an insect cell for baculovirus expression, or a procaryotic cell such as a bacteria cell, for example E. coli. When the host cell is grown under conditions which favor expression of the inserted nucleic acid molecule, the polypeptide is biosynthetically produced and is isolated by methods well known to those of skill in the art. This invention also encompasses these polypeptides.

A composition comprising the isolated somatotropin polypeptides of this invention and a pharmaceutically acceptable carrier is provided by this invention. As used herein, the term "pharmaceutically acceptable" carrier encompasses any of the standard pharmaceutical carriers, such as phosphate buffered saline solution, water, emulsions, such as oil/water emulsions, and various types of wetting agents. The preferred compositions of this invention contain porcine somatotropin polypeptides.

These compositions are particularly useful to enhance the biological activity of growth hormone in an animal. The composition is administered to the animal in an effective biological enhancing amount, the precise amount depending on the size of animal being treated. Methods of determining the amount are well known to those of skill in the art.

These compositions also are useful to induce antigrowth hormone antibodies in an animal by administering to the animal an effective immunizing amount of these compositions. As noted above, the precise amount administered depends on the size and species of animal being treated, nevertheless, methods of determining the amount are well known to those of skill in the art. These amounts range, for example, from about 1 ug to about 10 mg of pST. However, in the preferred embodiment of this invention, the amount is in the range of about 3 ug to about 5 mg pST.

The growth of an animal also is enhanced by administering to the animal an effective growth-enhancing amount of these compositions. Again, the precise amount to be administered is determined by one of skill in the art by well known methods. These amounts range, for example, from about 1 ug to about 10 mg. However, in the preferred embodiment of this invention, the amount is in the range of about 3 ug to about 5 mg of the composition.

Animals which are treated by the above methods include, but are not limited to cattle, pigs, goats, chickens, turkeys, geese, rabbits and vertebrates, such as fish. For the purposes of this invention, administration means administration orally, intravenously or intrperitoneally.

Some embodiments of this invention are detailed below. However, the metes and bounds of this invention are not to be limited by the following examples.

EXAMPLE 1

Animals and Synthesis of Peptides

Hypophysectomized female Sprague-Dawley rats, 21 days of age and weighing 50–64 g, are obtained from Taconic Farm, Germantown, N.Y. and used to assay for Growth Hormone (GH). Female crossbred swine (Duroc x Yorkshire x Hampshire), 3–5 months of age, weighing 30–50 kg, are obtained from the breeding colony of American Cyanamid Co., Princeton, N.J. and used for the production of antibodies.

Figure 6:
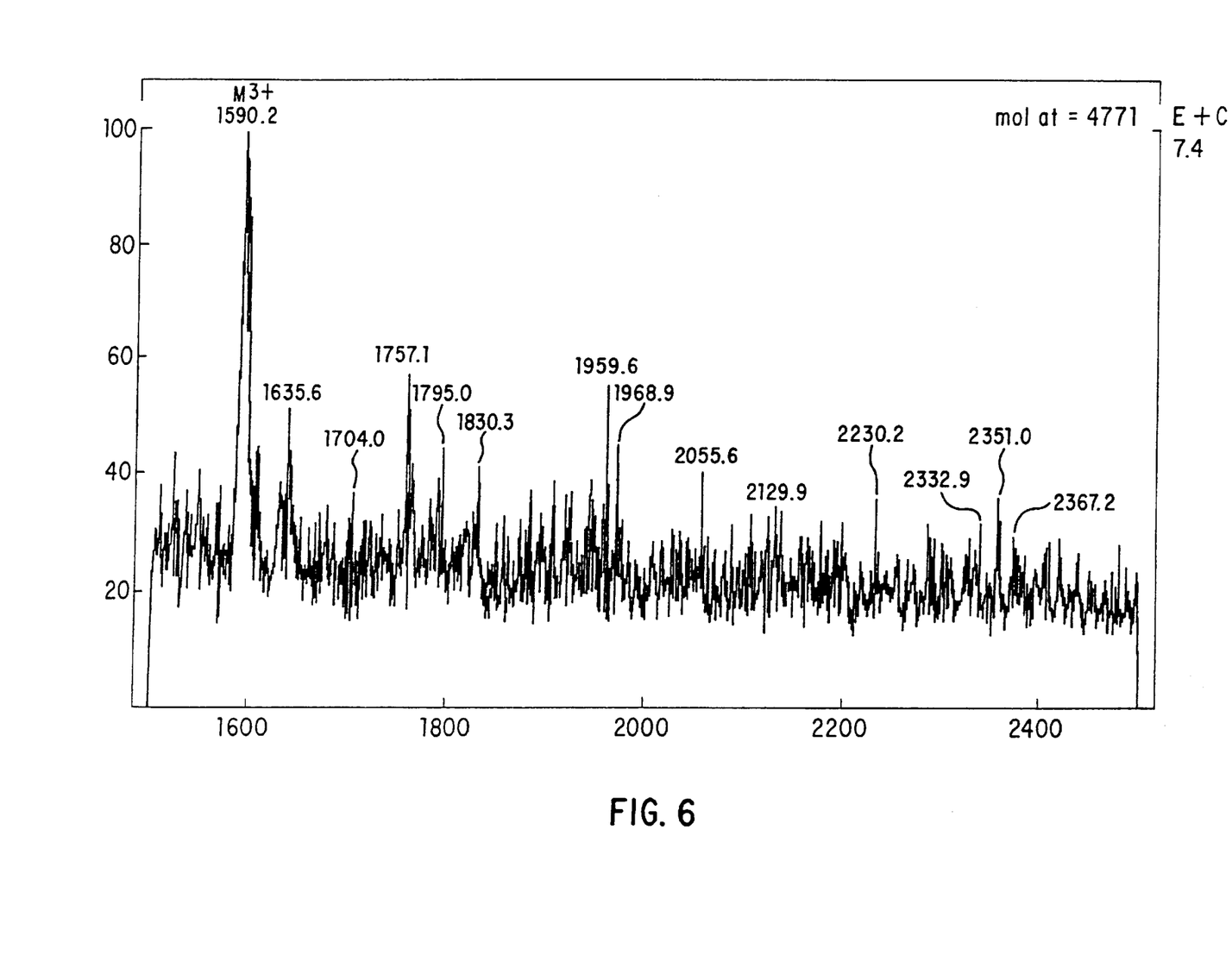
FIG. 6 is the mass spectrometric analysis of purified pST.

A peptide with the sequence of Phe-Ser-Glu-Thr-Ile-Pro-Ala-Pro-Thr-Gly-Lys-Asp-Glu-Ala-Gln-Gln-Arg-Ser-Asp-Val-Glu-Leu-Leu-Arg-Phe-Ser-Leu-Leu-Leu-Ile-Gln-Ser-Trp-Leu-Gly-Pro-Val-Gln-Phe-Leu-Ser-Arg, corresponding to amino acid positions at 54 to 95 of Sequence I.D. No. 1, is synthesized by a Milligen-Bioserch 9600 Automatic Peptide Synthesizer (Millipore, Bedford, Mass.) using 9-fluoroenylmethyloxycarbonyl ("Fmoc")amino acid with Benzotriazol-1-yloxytri(dimethylamino)phosphonium hexafluorophosphate ("BOP"), 1-hydroxybenzotriazole ("HOBT") as coupling reagents and 4-hydroxymethyl-phenoxy-resin as carrier. For side chain protection, the following Fmoc-amino acid derivatives are used: Fmoc-Ser (t-Bu), Fmoc-Thr(t-Bu), Fmoc-Arg(Pmc), Fmco-Lys(Boc), Fmoc-Gln-oPfp and Fmoc-Asp(O-t-Bu). After the solid phase peptide synthesis, the peptide is liberated from the resin by treating with 95% TFA, 2.5% anisole and 2.5% ethanedithiol; then precipitated from cooled ether solution. The crude peptide is then purified by preparative HPLC C18 column (Rainin, Woburn, Mass.) using water-acetonitrile gradient (30–80%) in 25 min; flow rate at 22 ml/min. The purity of this peptide may be determined by standard amino acid analysis and FAB mass spectrometry (see FIG. 6).

EXAMPLE 2

Conlugation of Peptide with Carrier

The peptide identified above is conjugated to ovalbumin using 2% glutaldehyde at room temperature (approximately 25° C.) and followed by reduction with $NaBH_4$. The excess $NaBH_4$ is quenched by acetic acid and the conjugate is purified by sizing column chromatography. It is lyophilized and stored at −20° C. until use.

EXAMPLE 3

Production of Antibodies to Peptides

The peptide-ovalbumin conjugates are emulsified with complete Freund's adjuvant and injected subcutaneously into the neck area behind the ears of pigs. All animals are boosted at least twice with the same antigens every 4 weeks, and blood samples were taken 7–14 days after the last boosting. Serum is obtained after clotting and immunoglobulin (Ig) is purified by a preparative Protein A Sepherose HR 16/5 column on a fast protein liquid chromatography (FPLC) system (Pharmacia) or ammonium sulfate precipitation. The antibodies are stored in aliquots at −80° C. until used.

EXAMPLE 4

Solid Phase Enzyme-linked Immunoabsorbent Assay (ELISA) and Method to Determine Analogues of PST As an example, antigen is prepared in phosphate-buffered saline (PBS) and 1 ug in 100 ul is added to each well of a 96-well-flat-bottom polystyrene plate. After being incubated for 1 hour, the plate is washed three times with PBS containing 0.05% (v/v) Tween-20 by an automatic plate washer (Dynatech Wash II, Chantilly, Va., U.S.A.) and each well is dispensed with 200 ul of 2% (w/v) bovine serum albumin (Sigma). The plate is incubated again for another hour. Serum samples are added. These are tested at a final concentration of 5% in the wells. The plate is incubated for 30 min, washed six times with PBS, and 100 ul of alkaline phosphatase-conjugated goat anti-rabbit IgG F(ab')$_2$(Zymed Laboratories, South San Francisco, Calif., U.S.A.) is added. The plate is washed again after a 30 minute incubation and 100 ul p-nitrophenyl phosphate (Sigma) in 0.1M diethanolamine (pH 10.3) is added as substrate for color development. Finally, the colorimetric response is recorded as optical density (OD) by an ELISA plate reader at a wavelength of 405 nm. The incubation procedure is always performed at 37° C.

Figure 5A:
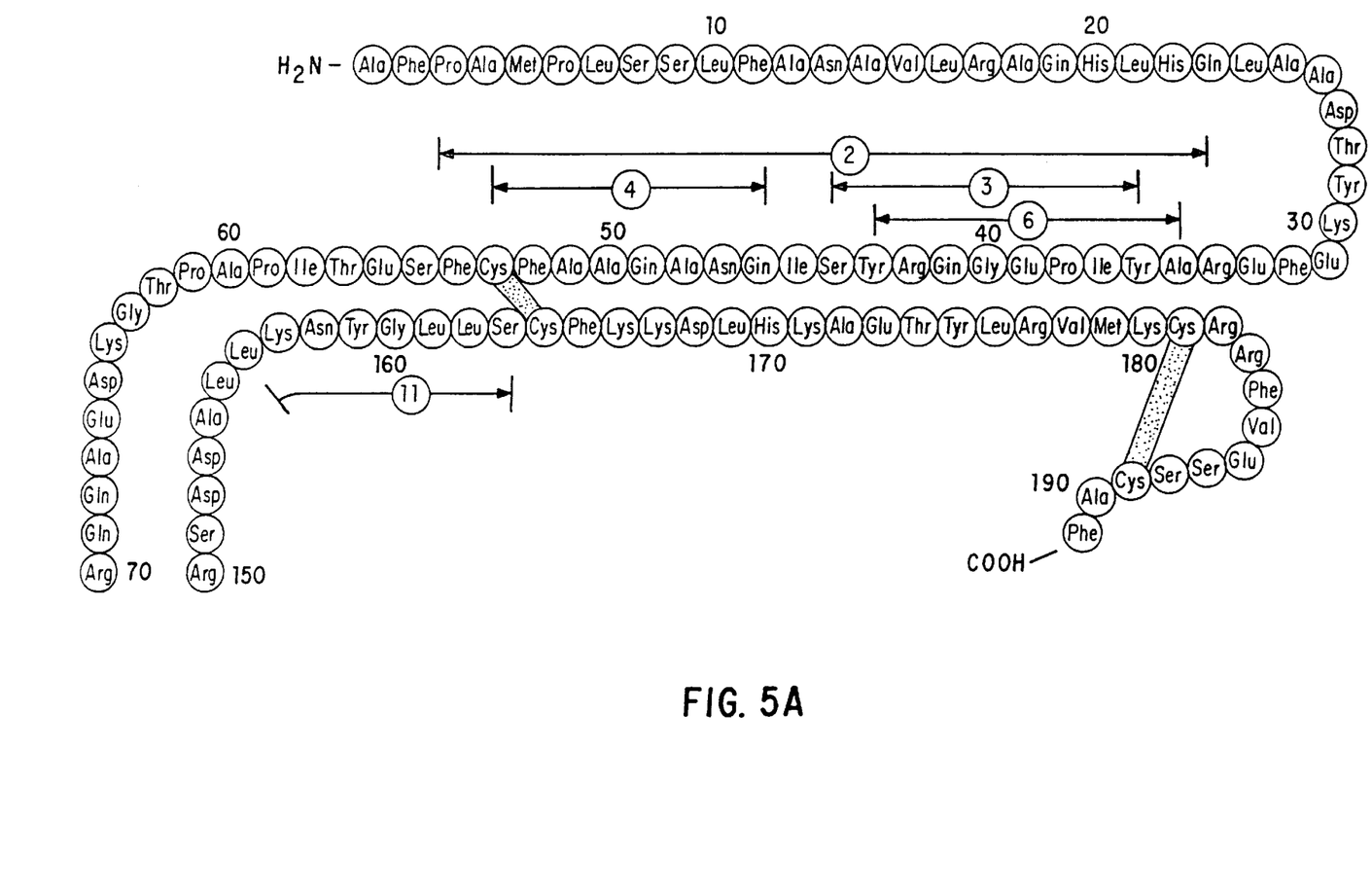
FIG. 5 shows the amino acid sequence of porcine somatotropin. Also shown as sequence I.D. No. 1.
Figure 5B:
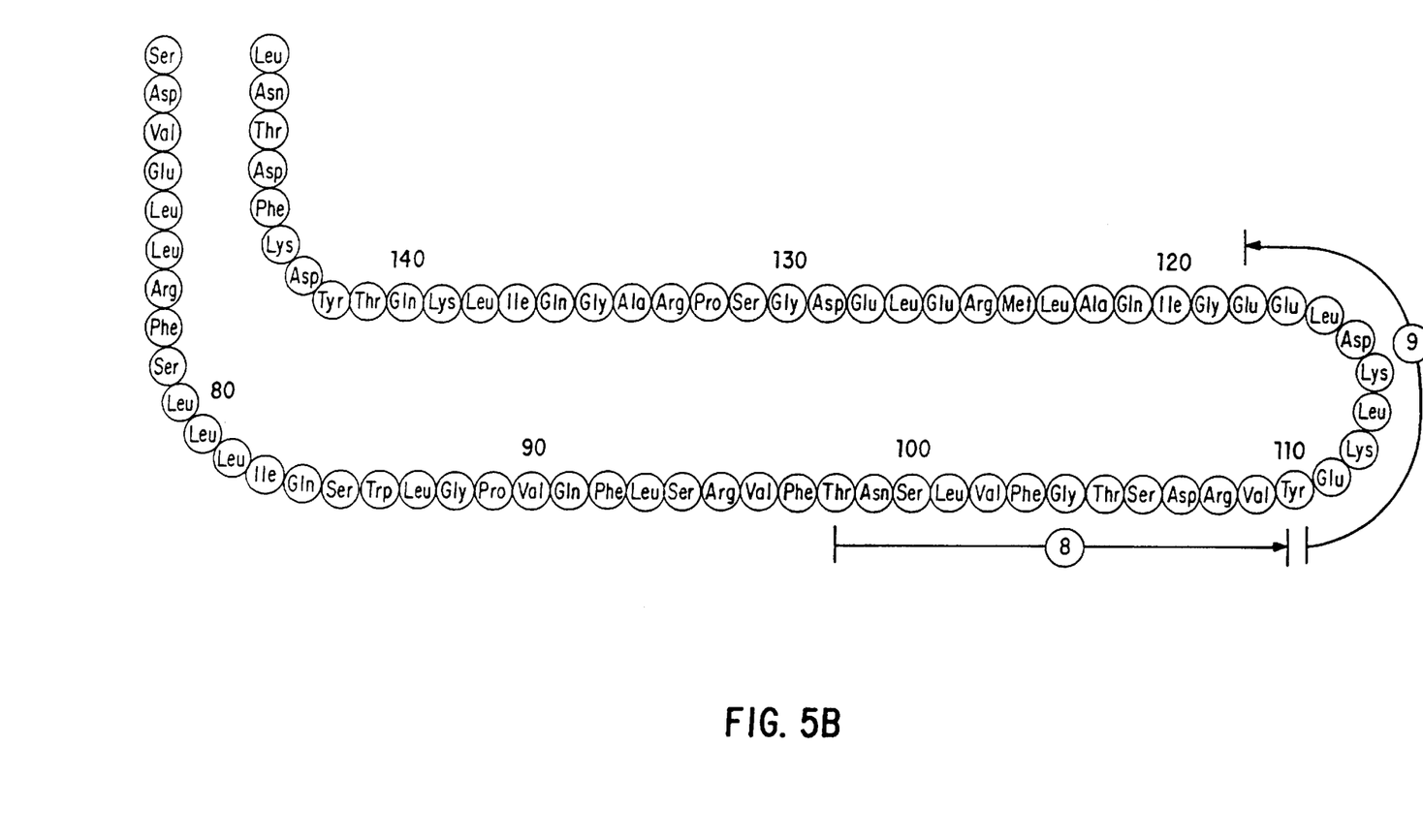

This method is used to detect analogues of pST of native pST shown in FIG. 5. Using this method, samples of polypeptides are prepared in PBS and aliquoted onto 96-well plates. Native pST (54-95) is used as the control.

EXAMPLE 5

Biological Assays for Growth-Promoting Activity

Hypophysectomized rats are randomly allocated to groups of eight. Antibody mixed with 5 ug pST at room temperature for 1 hour is administered subcutaneously in the neck region of experimental rats. All animals are treated daily for various periods of time and their growth is recorded as net weight gain. Statistical evaluation is carried out by comparing with pST treatment alone using the least-squares analysis of variance for randomized design using the General Linear Models procedure of the Statistical Analysis System.

EXAMPLE 6

Production of Antibodies to PST Peptides

Figure 1:
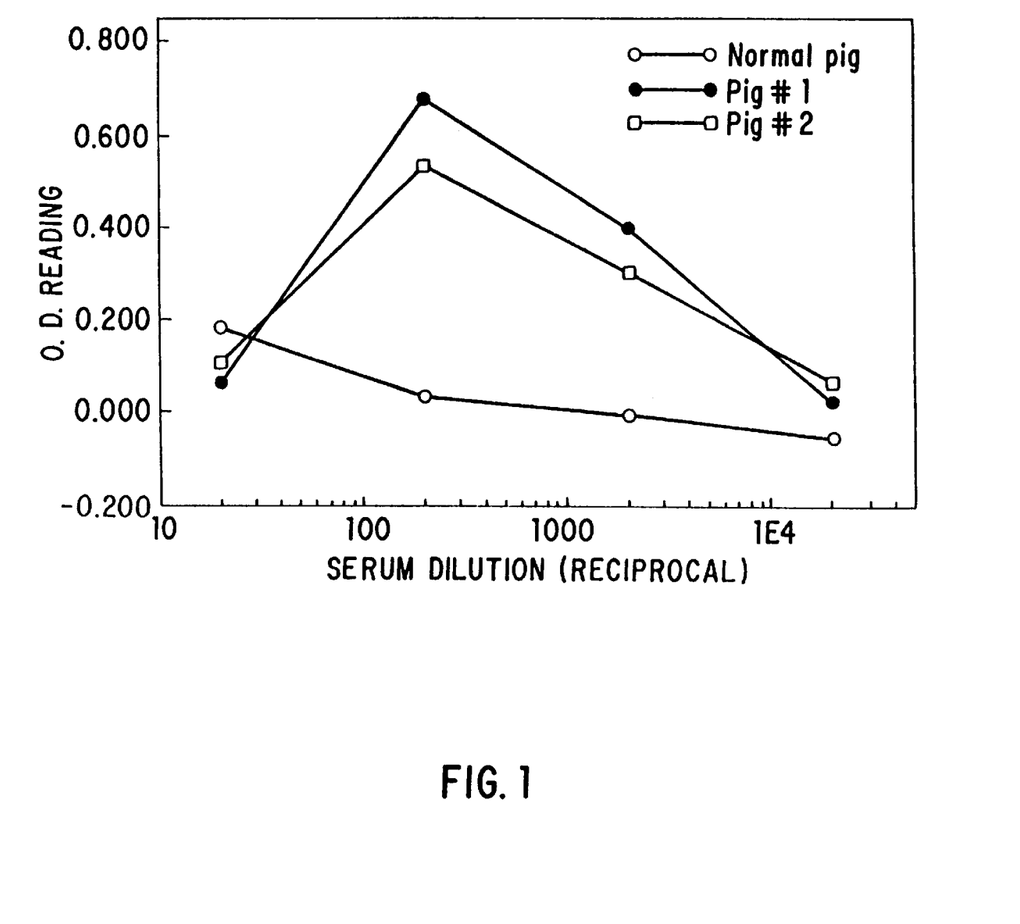
FIG. 1 shows the results of the following ELISA assay. An ELISA plate is coated with pST and serum samples from two pigs, both which are immunized with pST (54-95), and added in the plate to determine anti-pST antibody titers. Serum from pooled untreated normal pigs is similarly tested as control.
Figure 2:
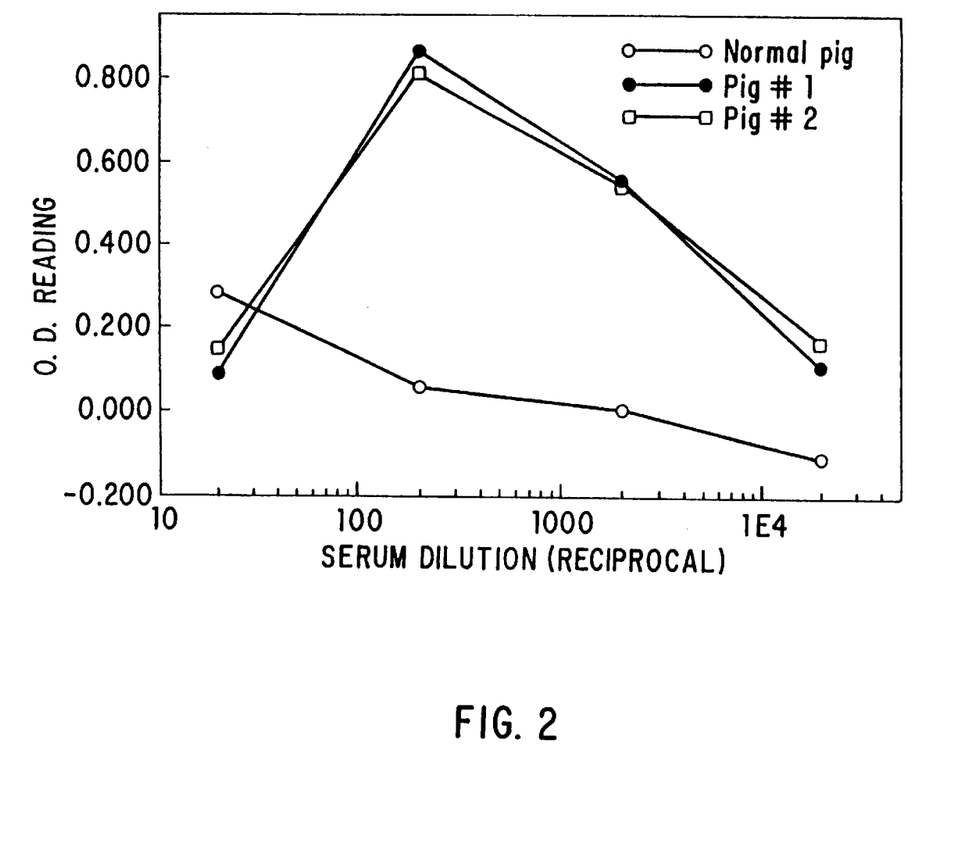
FIG. 2 shows the results of the following ELISA assay. ELISA plate is coated with peptide pST (54-95) and serum samples from two pigs, both which are immunized with pST (54-95), are added in the plate to determine anti-pST antibody titers. Serum from pooled untreated normal pigs is similarly tested as control.

The peptide pGH(54-95) (also corresponding to amino acid positions 54 to 95 of Sequence I.D. No. 1) is chemically conjugated to ovalbumin. The conjugates are mixed with Freund's adjuvant and injected into two pigs. Sera from these pigs are obtained after two antigen boostings and tested for antibody titers in ELISA. As indicated in FIG. 1, sera from these pigs contain antibodies immunoreactive with pST. Normal pooled pig serum is found to be inactive. All these serum samples are similarly tested against pST (54-95) peptide as target and found that both immunized pigs generate anti-peptide antibody, whereas untreated normal pigs show very little, if there is any, titer (FIG. 2).

EXAMPLE 7

Biological Activity of Antibody to pST (54-95)

Figure 3:
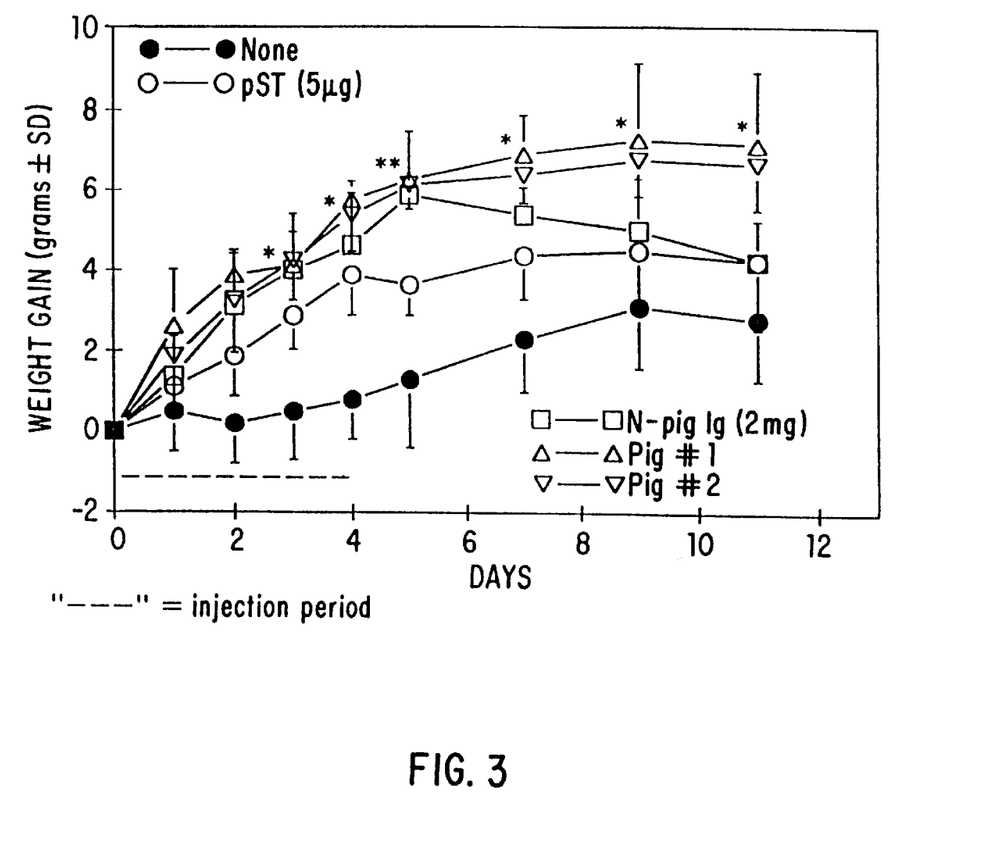
FIG. 3 shows the biological activity of antibody to pST (54-95). Hypox rats are injected subcutaneously with pST (5 ug/day) with or without antibody (2 mg/day) for 5 consecutive days and the net weight gain is recorded. Immune antibodies are prepared from two pigs that had been immunized with pST (54-95) and the control antibody is prepared from a pooled sera of non-immunized pigs. *,p<0.05; **,p<0.01.

The growth enhancing effect of these antibodies are evaluated in hypox rats. Hypox rats are injected subcutaneously with pST (5 ug) with or without antibody for 5 consecutive days (day 0 to 4). Net weight gains are recorded. Two different sources of experimental antibodies are prepared from two pigs that are immunized with pST (54-95), and the control antibody prepared from a pooled sera of non-immunized pigs. Results in FIG. 3 indicate that at a 2 mg dose, all antibodies including non-immune antibody increase the activity of pST in promoting hypox rats to grow. However, the effect of non-immune antibody is short-lived, whereas in the two pigs, antibodies manifest an apparently longer effect.

Figure 4:
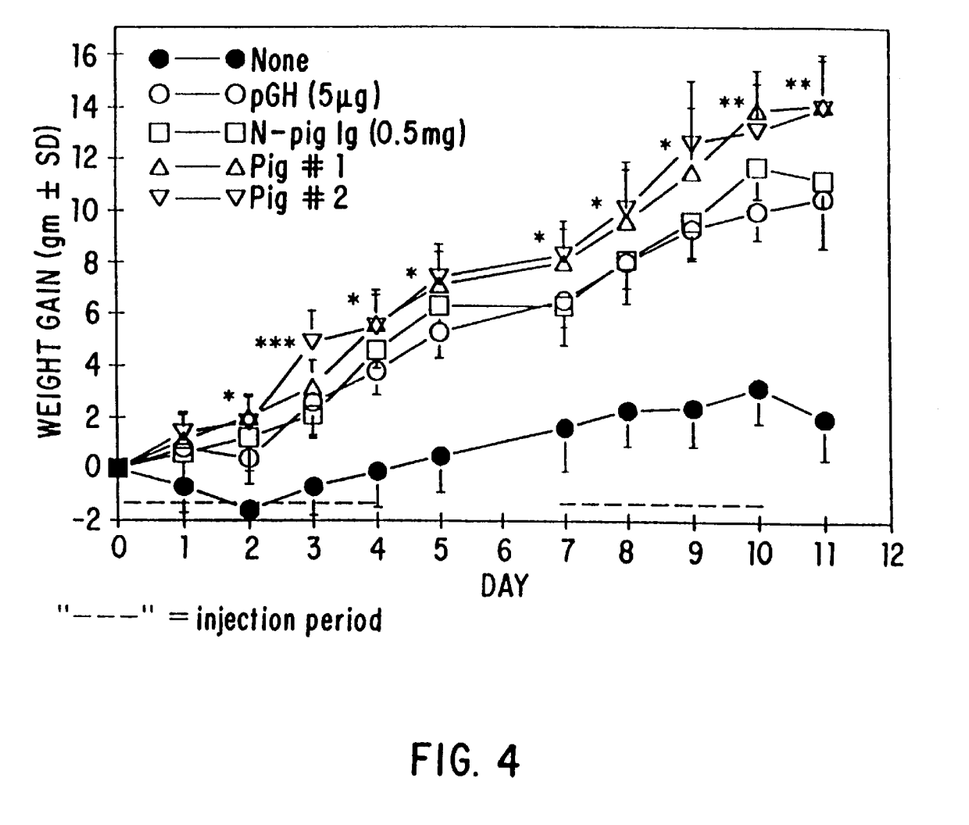
FIG. 4 shows the biological activity of antibody to pST (54-95). In a study similar to that shown in FIG. 3, except antibody is injected at a dose of 0.5 mg/day and for a longer period of time. *,p<0.05; ,p<0.01; *,p<0.001.

A second experiment is carried out at a lower antibody dose and for a longer period of time. Animals are treated with 5 ug/day pST from day 0 to 4 and again from day 7 to 10 show a marked growth as compared to untreated rats (FIG. 4). Addition of immune antibodies (0.5 mg/day) from these two pigs significantly enhance the effect of pST, whereas antibody from pooled normal pig sera is ineffective. These data show that pST (54-95) renders pigs able to produce antibodies capable of enhancing pST activity.

EXAMPLE 8

Insertion of Nucleic Acid Encoding PST Polypeptide into Expression Vectors

The nucleotide sequence coding for the pST polypeptide is inserted into an appropriate expression vector, i.e; a vector that contains the necessary elements for the transcription and translation of the inserted protein-coding sequence. The coding sequence may be extended at either the 5' or 3' terminus or both termini to extend biosynthetically the polypeptide while retaining the epitope. The extension may provide an arm for linking, e.g., to a label, to a carrier or surface.

A variety of host-vector systems are utilized to express the pST sequence. These include, but are not limited to, mammalian cell cultures such as Chinese hamster ovary cell host cultures (CHO); mammalian systems infected with virus (e.g., vaccinia virus, adenovirus); insect cell systems infected with virus (e.g., baculovirus); microorganisms such as yeast containing yeast vectors or bacteria transformed with bacteriophage DNA, plasmid DNA or cosmid DNA. When cloning in mammalian cell systems, promoters isolated from the genome of mammalian cells (mouse metallothionine promoter) or from viruses that grow in these cells, (vaccinia virus 7.5K promoter) is used. In some embodiments of this invention, promoters are produced by recombinant DNA or synthetic techniques to provide for transcription of the inserted sequence.

Specific initiation signals are provided for efficient translation of inserted nucleotides. These signals include the ATG initiation codon and adjacent sequences, and are inserted in phase with the reading frame of the pST sequence to ensure translation of the entire insert. These exogenous translational control signals and initiation codons are from a variety of origins, both natural and synthetic. The pST nucleotides are inserted into the vectors by in vitro recombinant techniques and by in vivo recombination.

Expression vectors containing the pST sequences are identified, for example, by three general approaches: 1) DNA-DNA hybridization, 2) presence or absence of marker gene functions and 3) expression of the inserted pST sequences. In the first approach, the presence of inserted pST sequences in an expression vector are detected by DNA-DNA hybridization using probes comprising sequences that are homologous to the pST nucleotides. In the second approach, the recombinant vector/host system is identified and selected based upon the presence or absence of certain "marker" gene functions (e.g., thymidine kinase activity, resistance to antibiotics, transformation phenotype) caused by the insertion of the foreign genes in the vector. In the third approach, recombinant expression vectors are identified by assaying the foreign gene product expressed by the recombinant, for example, by assaying for the reactivity of the nucleotide product with antibody PS-7.6.

In addition, the host cell strain may be chosen that modulated the expression of the inserted pST sequences. Expression from certain promoters is elevated in the presence of certain inducers, (e.g., zinc and cadmium ions for metallothionine promoters).

After a particular recombinant DNA molecule is identified and isolated, several methods are used to propagate it, depending on whether such a recombinant constitutes a self-replicating unit (a replicon). A self-replicating unit, a plasmid, a virus, a cell, can multiply itself in the appropriate cellular environment and growth conditions. Recombinants that lack the self-replicating unit are integrated into a molecule having such a unit so that it is propagated. For example, certain plasmid expression vectors upon introduction into a host cell need to be integrated into the cellular chromosome to ensure propagation and stable expression of the recombinant gene. After a suitable host system and growth conditions are established, recombinant expression vectors are propagated and prepared in quantity.

EXAMPLE 9

E. coli as an Expression Vector

Many E. coli plasmids are known and have been used to express foreign genes. For economic reasons, it is highly preferable to be able to obtain a high level of expression. One way to obtain large amounts of a given gene product is to clone a gene on a plasmid that has a very high copy number within the bacterial cell. By increasing the number of copies of a particular gene, mRNA levels would normally also increase, which in turn leads to increased production of the desired protein.

EXAMPLE 10

Vaccinia Virus as an Expression Vector

Vaccinia virus may be used as a cloning and expression vector. The virus contains a linear double-stranded DNA genome of approximately 187 kb pairs and replicates within the cytoplasm of infected cells. These viruses contain a complete transcriptional enzyme system (including capping, methylating and polyadenylating enzymes) within the virus core. This system is necessary for virus infectivity because vaccinia virus transcriptional regulatory sequences (promoters) allow for initiation of transcription by vaccinia RNA polymerase, but not by cellular RNA polymerase.

Expression of foreign DNA in recombinant viruses requires the fusion of vaccinia promoters to polypeptide coding sequences of the foreign nucleotide. Plasmid vectors, also called insertion vectors, are used to insert the chimeric gene into vaccinia virus. One type of insertion vector comprises: 1) a vaccinia virus promoter including the transcriptional initiation site; 2) several unique restriction endonuclease cloning sites downstream from the transcriptional start site for insertion of foreign DNA fragments; 3) nonessential vaccinia virus DNA (such as the thymidine kinase gene) flanking the promoter and cloning sites that direct insertion of the chimeric gene into the homologous nonessential region of the virus genome; and 4) a bacterial origin of replication and antibiotic resistance marker for replication and selection in E. coli.

Recombinant viruses are produce by transfection of recombinant bacterial insertion vectors containing the foreign gene into cells infected with vaccinia virus. Homologous recombination takes place within the infected cells and results in the insertion of the foreign gene into the viral genome. See for example, U.S. Pat. No. 4,603,112, the contents of which are hereby incorporated by reference into the present disclosure. Immunological techniques, DNA plaque hybridization or genetic selection, for example, is used to identify and isolate the desired recombinant virus. These vaccinia virus retain the functions essential for infectivity and are constructed to accommodate up to approximately 35 db of foreign DNA.

EXAMPLE 11

Baculovirus as an Expression Vector

A baculovirus, such as Autographica californica nuclear polyhedris virus (AcNPV) is used as a cloning or expression vector. The infectious form of ACNPV is normally found in a viral occlusion. This structure is largely composed of polyhedron polypeptide in which virus particles are embedded. Polyhedron gene expression occurs very late in the infection cycle, after mature virus particles are formed. Therefore, polyhedron gene expression is a dispensable function, i.e., non-occluded virus particles produced in the absence of polyhedron gene expression are fully active and are capable of infecting cells in culture. For the purposes of illustration only, a recombinant baculovirus can be prepared in two steps. First, baculovirus DNA is cleaved to produce a fragment comprising a polyhedron gene or a portion thereof, which is then inserted into a cloning vehicle. The gene to be expressed is also inserted into the cloning vehicle, and it is so inserted so that it is under control of the polyhedron promoter. This recombinant molecule may be termed the recombinant transfer vector. Normally, the recombinant transfer vector is amplified in appropriate host cells. The recombinant transfer vector is mixed with baculovirus helper DNA and used to transfect insect cells in culture to effect recombination and incorporation of the cloned gene at the polyhedron gene locus of the baculovirus genome. The resultant recombinant baculovirus is used to infect susceptible insects or cultured insect cells.

What is claimed is:

1. An isolated polypeptide encoding an epitope for porcine somatotropin (pST) having an amino acid sequence shown in Sequence ID 1, wherein said sequence is selected from the group consisting of (i) a sequence from amino acid number 54 to amino acid number 95 and (ii) a sequence from amino acid number 80 to amino acid number 90.

2. A composition comprising the isolated polypeptide of claim 1 and a pharmaceutically acceptable carrier.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:

```
        (A) LENGTH: 191 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

Ala Phe Pro Ala Met Pro Leu Ser Ser Leu Phe Ala Asn Ala Val Leu
   1               5                   10                  15

Arg Ala Gly His Leu His Gln Leu Ala Ala Asn Thr Tyr Lys Glu Phe
                   20                  25                  30

Glu Arg Ala Tyr Ile Pro Glu Gly Gln Arg Tyr Ser Ile Gln Asn Ala
                   35                  40                  45

Gln Ala Ala Phe Cys Phe Ser Glu Thr Ile Pro Ala Pro Thr Gly Lys
               50                  55                  60

Asp Glu Ala Gln Gln Arg Ser Asn Val Glu Leu Leu Arg Phe Ser Leu
   65                  70                  75                  80

Leu Leu Ile Gln Ser Trp Leu Gly Pro Val Gln Phe Leu Ser Arg Val
                   85                  90                  95

Phe Thr Asn Ser Leu Val Phe Gly Thr Ser Asp Arg Val Tyr Glu Lys
                   100                 105                 110

Leu Lys Asp Leu Glu Glu Gly Ile Gln Ala Leu Met Arg Glu Leu Glu
                   115                 120                 125

Asp Gly Ser Pro Arg Ala Gly Glu Ile Leu Lys Gln Thr Tyr Asp Lys
                   130                 135                 140

Phe Asp Thr Asn Leu Arg Ser Asp Asp Ala Leu Leu Lys Asn Tyr Gly
   145                 150                 155                 160

Leu Leu Ser Cys Phe Lys Lys Asp Leu His Lys Ala Glu Thr Tyr Leu
                   165                 170                 175

Arg Val Met Lys Cys Arg Arg Phe Val Gln Ser Ser Cys Ala Phe
                   180                 185                 190
```